United States Patent [19]

Cohen

[11] Patent Number: 5,830,810
[45] Date of Patent: Nov. 3, 1998

[54] NONWOVEN BARRIER AND METHOD OF MAKING THE SAME

[75] Inventor: Bernard Cohen, Berkeley Lake, Ga.

[73] Assignee: Kimberly-Clark Worldwide, Inc., Neenah, Wis.

[21] Appl. No.: 802,500

[22] Filed: Feb. 20, 1997

Related U.S. Application Data

[63] Continuation of Ser. No. 504,209, Jul. 19, 1995, abandoned.

[51] Int. Cl.$^6$ .......................... B01D 39/16; B01D 53/32; B29C 71/04; B03C 9/00; B32B 33/00
[52] U.S. Cl. .......................... 442/110; 2/901; 53/111 R; 55/524; 55/528; 55/DIG. 5; 55/DIG. 39; 128/206.19; 128/849; 204/165; 204/168; 264/423; 264/483; 264/DIG. 48; 427/446; 427/458; 427/538; 428/311.5; 428/409; 428/903; 442/114; 442/382; 442/414
[58] Field of Search .................................. 2/901; 55/524, 55/528, DIG. 5, DIG. 39; 128/206.19, 849; 204/165, 168; 264/423, 483, DIG. 48; 427/446, 458, 538; 428/311.5, 409, 903; 442/110, 114, 382, 414

[56] References Cited

U.S. PATENT DOCUMENTS

| | | |
|---|---|---|
| Re. 30,782 | 10/1981 | van Turnhout .............................. 264/22 |
| Re. 31,285 | 6/1983 | van Turnhout et al. ................... 55/155 |
| Re. 32,171 | 6/1986 | van Turnhout .............................. 55/155 |
| 668,791 | 2/1901 | Blake et al. . |
| 2,748,018 | 5/1956 | Miller . |
| 2,998,051 | 8/1961 | Sittel ........................................ 154/1.7 |
| 3,059,772 | 10/1962 | Baron ...................................... 209/127 |
| 3,125,547 | 3/1964 | Blatz ....................................... 260/45.5 |
| 3,281,347 | 10/1966 | Winder ................................... 204/168 |
| 3,323,933 | 6/1967 | Barford et al. . |
| 3,338,992 | 8/1967 | Kinney ...................................... 264/24 |
| 3,341,394 | 9/1967 | Kinney . |
| 3,436,797 | 4/1969 | Graf et al. ............................ 156/272.6 |
| 3,502,763 | 3/1970 | Hartmann ................................ 264/210 |
| 3,542,615 | 11/1970 | Dobo et al. .............................. 156/181 |
| 3,692,606 | 9/1972 | Miller et al. .......................... 156/273.1 |
| 3,692,618 | 9/1972 | Dorschner et al. . |
| 3,802,817 | 4/1974 | Matsuki et al. ........................... 425/66 |
| 3,821,021 | 6/1974 | McMilllin . |
| 3,849,241 | 11/1974 | Butin et al. . |
| 3,855,046 | 12/1974 | Hansen . |
| 3,859,330 | 1/1975 | Proskow .............................. 260/47 UA |
| 3,896,802 | 7/1975 | Williams ................................. 128/156 |
| 3,907,604 | 9/1975 | Prentice .................................. 136/146 |
| 3,909,009 | 9/1975 | Cvetko et al. ............................ 274/37 |
| 3,962,386 | 6/1976 | Driscoll ..................................... 264/22 |
| 3,979,529 | 9/1976 | Rebentisch et al. ....................... 427/25 |
| 3,998,916 | 12/1976 | van Turnhout ............................ 264/22 |
| 4,011,067 | 3/1977 | Carey, Jr. ................................. 55/354 |
| 4,013,816 | 3/1977 | Sabee et al. ............................ 428/288 |
| 4,035,164 | 7/1977 | Taylor . |
| 4,041,203 | 8/1977 | Brock et al. ............................ 428/157 |
| 4,058,724 | 11/1977 | McKinney et al. . |
| 4,070,218 | 1/1978 | Weber .................................... 156/167 |
| 4,091,140 | 5/1978 | Harrnon . |
| 4,096,289 | 6/1978 | Nischwitz et al. ......................... 427/32 |
| 4,103,062 | 7/1978 | Aberson et al. ......................... 428/283 |
| 4,140,607 | 2/1979 | Kreiseimeier et al. ................. 204/168 |
| 4,170,304 | 10/1979 | Huke . |
| 4,178,157 | 12/1979 | van Turnhout et al. .................. 55/155 |
| 4,185,972 | 1/1980 | Nitta et al. . |
| 4,196,245 | 4/1980 | Kitson et al. ............................ 428/198 |
| 4,208,366 | 6/1980 | Kinney . |
| 4,209,563 | 6/1980 | Sisson .................................... 428/288 |
| 4,215,682 | 8/1980 | Kubik et al. ....................... 128/205.29 |
| 4,223,677 | 9/1980 | Anderson ............................... 128/287 |
| 4,273,635 | 6/1981 | Beraud et al. .......................... 204/165 |
| 4,298,440 | 11/1981 | Hood ...................................... 204/165 |
| 4,307,143 | 12/1981 | Meitner .................................... 252/91 |
| 4,308,223 | 12/1981 | Stern ....................................... 264/22 |
| 4,310,478 | 1/1982 | Balslev et al. . |
| 4,323,374 | 4/1982 | Shinagawa et al. . |
| 4,324,198 | 4/1982 | Muz ........................................ 118/630 |
| 4,340,563 | 7/1982 | Appel et al. ............................ 264/518 |
| 4,342,812 | 8/1982 | Selwood ................................. 428/286 |
| 4,353,799 | 10/1982 | Leonard ............................... 210/321.3 |
| 4,363,682 | 12/1982 | Thiebault . |
| 4,373,224 | 2/1983 | Bandai et al. . |
| 4,374,888 | 2/1983 | Bornslaeger ............................ 428/198 |
| 4,375,718 | 3/1983 | Wadsworth et al. ...................... 29/592 |
| 4,392,876 | 7/1983 | Schmidt . |

(List continued on next page.)

FOREIGN PATENT DOCUMENTS

| | | |
|---|---|---|
| 1188452 | 6/1985 | Canada . |
| 0 125 851 | 11/1984 | European Pat. Off. .......... D21C 9/00 |
| 0 156 160 | 10/1985 | European Pat. Off. ........ A61L 15/00 |
| 0334829 | 9/1989 | European Pat. Off. . |
| 0337662A3 | 10/1989 | European Pat. Off. . |
| 0 375 234 | 6/1990 | European Pat. Off. . |
| 0 391 725 | 10/1990 | European Pat. Off. . |
| 0444671A1 | 9/1991 | European Pat. Off. . |
| 0462574 | 12/1991 | European Pat. Off. . |
| 0 478 011 | 4/1992 | European Pat. Off. ........ A61F 13/15 |
| 0 497 072 | 8/1992 | European Pat. Off. ........ A61F 13/15 |
| 0 520 798 | 12/1992 | European Pat. Off. ......... D04H 1/42 |

(List continued on next page.)

OTHER PUBLICATIONS

An introduction to Electrostatic Separation, Technical Bulletin, Bulletin 8570, Carpco, Inc.
Electrostatic Separation of Mixed Granular Solids by Oliver C. Ralston, Elsevier Publishing Company, 1961, Chapter IV, "Applications of Electrostatic Separation", pp. 134–234.
Search Report for PCT/US95/15488 dated Nov. 10, 1996.

(List continued on next page.)

Primary Examiner—James C. Cannon
Attorney, Agent, or Firm—David J. Alexander; Jones & Askew, LLP

[57] ABSTRACT

A plasma sterilizable fabric which is subjected to charging, for example electrostatic charging, is provided. Plasma sterilizable fabrics may include nonwovens and laminate nonwovens. The plasma sterilizable fabrics may also be treated with an antistatic material before or after subjecting the same to charging.

33 Claims, No Drawings

U.S. PATENT DOCUMENTS

| | | |
|---|---|---|
| 4,394,235 | 7/1983 | Brandt et al. . |
| 4,411,795 | 10/1983 | Olson ................................. 210/679 |
| 4,430,277 | 2/1984 | Lin . |
| 4,443,513 | 4/1984 | Meitner et al. ...................... 422/195 |
| 4,443,515 | 4/1984 | Atlas ................................... 428/224 |
| 4,451,589 | 5/1984 | Morman et al. ..................... 523/124 |
| 4,455,195 | 6/1984 | Kinsley ............................... 162/13 |
| 4,455,237 | 6/1984 | Kinsely ............................... 210/767 |
| 4,456,648 | 6/1984 | Adamse et al. ..................... 428/283 |
| 4,492,633 | 1/1985 | Sandulyak et al. . |
| 4,507,539 | 3/1985 | Sando et al. ................... 219/121 PY |
| 4,513,049 | 4/1985 | Yamasaki et al. . |
| 4,517,143 | 5/1985 | Kisler . |
| 4,534,918 | 8/1985 | Forrest, Jr. . |
| 4,551,378 | 11/1985 | Carey, Jr. ............................ 428/198 |
| 4,554,207 | 11/1985 | Lee ..................................... 428/288 |
| 4,555,811 | 12/1985 | Shimalla .............................. 2/51 |
| 4,588,537 | 5/1986 | Klaase et al. ....................... 264/22 |
| 4,592,815 | 6/1986 | Nakao ................................. 204/165 |
| 4,594,626 | 6/1986 | Frangesh . |
| 4,618,524 | 10/1986 | Groitzsch et al. ................... 428/198 |
| 4,622,259 | 11/1986 | McAmish et al. ................... 428/171 |
| 4,623,438 | 11/1986 | Felton et al. ........................ 204/168 |
| 4,626,263 | 12/1986 | Inoue et al. . |
| 4,652,282 | 3/1987 | Ohmori et al. ...................... 55/155 |
| 4,652,322 | 3/1987 | Lim ..................................... 156/181 |
| 4,657,639 | 4/1987 | Mahadevan et al. . |
| 4,657,804 | 4/1987 | Mays et al. .......................... 428/212 |
| 4,663,220 | 5/1987 | Wisneski et al. .................... 428/221 |
| 4,670,913 | 6/1987 | Morell et al. ........................ 2/227 |
| 4,671,943 | 6/1987 | Wahlquist . |
| 4,677,017 | 6/1987 | DeAntonis et al. ................. 428/214 |
| 4,689,241 | 8/1987 | Richart et al. ....................... 427/28 |
| 4,705,151 | 11/1987 | Eldridge . |
| 4,707,398 | 11/1987 | Boggs ................................. 428/224 |
| 4,714,647 | 12/1987 | Shipp, Jr. et al. ................... 428/212 |
| 4,720,415 | 1/1988 | Vander Wielen et al. .......... 428/152 |
| 4,738,772 | 4/1988 | Giesfeldt ............................. 209/2 |
| 4,739,882 | 4/1988 | Parikh et al. . |
| 4,749,348 | 6/1988 | Klaase et al. ....................... 425/174.8 |
| 4,761,326 | 8/1988 | Barnes et al. ....................... 428/219 |
| 4,789,504 | 12/1988 | Ohmori et al. . |
| 4,795,668 | 1/1989 | Krueger et al. ..................... 428/174 |
| 4,797,201 | 1/1989 | Kuppers et al. .................... 209/127.4 |
| 4,797,318 | 1/1989 | Brooker et al. . |
| 4,818,464 | 4/1989 | Lau ..................................... 264/510 |
| 4,826,703 | 5/1989 | Kisler ................................. 427/466 |
| 4,831,664 | 5/1989 | Suda . |
| 4,847,914 | 7/1989 | Suda . |
| 4,859,266 | 8/1989 | Akasaki et al. ..................... 156/273.1 |
| 4,863,785 | 9/1989 | Berman et al. ...................... 428/218 |
| 4,863,983 | 9/1989 | Johnson et al. ..................... 524/140 |
| 4,874,399 | 10/1989 | Reed et al. .......................... 55/2 |
| 4,874,659 | 10/1989 | Ando et al. .......................... 428/221 |
| 4,883,052 | 11/1989 | Weiss et al. . |
| 4,886,527 | 12/1989 | Fottinger et al. .................... 55/156 |
| 4,894,131 | 1/1990 | Jacobs et al. ....................... 204/165 |
| 4,901,370 | 2/1990 | Suda . |
| 4,904,174 | 2/1990 | Moosmayer et al. . |
| 4,917,942 | 4/1990 | Winters . |
| 4,920,168 | 4/1990 | Nohr et al. .......................... 524/188 |
| 4,944,854 | 7/1990 | Felton et al. ........................ 204/168 |
| 4,948,515 | 8/1990 | Okumura et al. ................... 210/748 |
| 4,948,639 | 8/1990 | Brooker et al. ..................... 428/35.2 |
| 4,960,820 | 10/1990 | Hwo .................................... 524/528 |
| 4,965,122 | 10/1990 | Morman ............................. 428/225 |
| 4,983,677 | 1/1991 | Johnson et al. ..................... 525/127 |
| 5,012,094 | 4/1991 | Hamade . |
| 5,021,501 | 6/1991 | Ohmori et al. ...................... 524/544 |
| 5,032,419 | 7/1991 | Lamirand et al. ................... 427/470 |
| 5,035,941 | 7/1991 | Blackburn .......................... 428/286 |
| 5,051,159 | 9/1991 | Togashi et al. ..................... 204/165 |
| 5,055,151 | 10/1991 | Duffy . |
| 5,057,710 | 10/1991 | Nishiura et al. .................... 307/400 |
| 5,062,158 | 11/1991 | Oka et al. ........................... 2/46 |
| 5,077,468 | 12/1991 | Hamade . |
| 5,090,975 | 2/1992 | Requejo et al. . |
| 5,110,620 | 5/1992 | Tani et al. ........................... 427/40 |
| 5,112,048 | 5/1992 | Deeds . |
| 5,112,677 | 5/1992 | Tani et al. . |
| 5,118,942 | 6/1992 | Hamade .............................. 250/324 |
| 5,135,724 | 8/1992 | Dinter et al. . |
| 5,138,971 | 8/1992 | Nakajima et al. . |
| 5,143,767 | 9/1992 | Matsuura et al. . |
| 5,149,335 | 9/1992 | Kellenberger et al. ............. 604/372 |
| 5,156,902 | 10/1992 | Pieper et al. ........................ 604/370 |
| 5,165,979 | 11/1992 | Watkins et al. ..................... 428/113 |
| 5,169,706 | 12/1992 | Collier, IV et al. ................ 428/152 |
| 5,173,356 | 12/1992 | Eaton et al. ......................... 428/219 |
| 5,178,932 | 1/1993 | Perkins et al. ...................... 428/198 |
| 5,183,701 | 2/1993 | Jacobs et al. ....................... 428/229 |
| 5,188,885 | 2/1993 | Timmons et al. ................... 428/198 |
| 5,204,174 | 4/1993 | Daponte et al. .................... 428/286 |
| 5,206,061 | 4/1993 | Ando et al. ......................... 428/34.7 |
| 5,213,881 | 5/1993 | Timmons et al. ................... 428/224 |
| 5,213,882 | 5/1993 | Sassa et al. ......................... 428/224 |
| 5,226,992 | 7/1993 | Morman .............................. 156/62.4 |
| 5,230,727 | 7/1993 | Pound et al. ........................ 55/492 |
| 5,232,770 | 8/1993 | Joseph ................................ 428/284 |
| 5,238,733 | 8/1993 | Joseph et al. ....................... 428/284 |
| 5,244,482 | 9/1993 | Hassenboehler, Jr. .............. 55/528 |
| 5,246,637 | 9/1993 | Matsuura et al. . |
| 5,247,072 | 9/1993 | Ning et al. .......................... 536/97 |
| 5,254,297 | 10/1993 | Deeds . |
| 5,256,176 | 10/1993 | Matsuura et al. ................... 55/528 |
| 5,257,982 | 11/1993 | Cohen et al. ....................... 604/378 |
| 5,264,276 | 11/1993 | McGregor et al. ................. 428/252 |
| 5,284,703 | 2/1994 | Everhart et al. .................... 428/283 |
| 5,286,326 | 2/1994 | Greve ................................. 156/272.4 |
| 5,294,482 | 3/1994 | Gessner . |
| 5,306,534 | 4/1994 | Bosses ................................ 428/35.2 |
| 5,308,674 | 5/1994 | Zafiroglu ............................ 428/102 |
| 5,308,691 | 5/1994 | Lim et al. ........................... 428/286 |
| 5,336,545 | 8/1994 | Morman .............................. 428/152 |
| 5,350,620 | 9/1994 | Sundet et al. ....................... 428/172 |
| 5,389,202 | 2/1995 | Everhart et al. .................... 162/103 |
| 5,397,413 | 3/1995 | Trimble et al. ..................... 156/167 |
| 5,401,446 | 3/1995 | Tsai et al. ........................... 264/22 |
| 5,407,581 | 4/1995 | Onodera et al. .................... 210/654 |
| 5,409,766 | 4/1995 | Yuasa et al. ........................ 428/224 |
| 5,411,576 | 5/1995 | Jones et al. ......................... 95/57 |
| 5,436,033 | 7/1995 | Mino et al. . |
| 5,436,066 | 7/1995 | Chen .................................. 428/288 |
| 5,441,550 | 8/1995 | Hassenboehler, Jr. .............. 55/486 |
| 5,443,606 | 8/1995 | Hassenboehler, Jr. .............. 55/486 |
| 5,455,108 | 10/1995 | Quincy et al. ...................... 428/266 |
| 5,456,972 | 10/1995 | Roth et al. .......................... 428/224 |
| 5,464,688 | 11/1995 | Timmons et al. . |
| 5,468,428 | 11/1995 | Hanschen et al. . |
| 5,472,481 | 12/1995 | Jones et al. ......................... 96/15 |
| 5,482,765 | 1/1996 | Bradley et al. . |
| 5,486,411 | 1/1996 | Hassenboehler, Jr. .............. 428/286 |
| 5,491,022 | 2/1996 | Smith .................................. 428/224 |
| 5,493,117 | 2/1996 | Tamaki et al. ...................... 264/483 |
| 5,496,507 | 3/1996 | Angadjivand et al. ............. 264/423 |
| 5,503,745 | 4/1996 | Ogata et al. ........................ 210/490 |
| 5,552,012 | 9/1996 | Morris et al. ....................... 156/272.4 |
| 5,620,785 | 4/1997 | Watt et al. ........................... 428/219 |
| 5,637,165 | 6/1997 | Chen .................................. 156/62.2 |

FOREIGN PATENT DOCUMENTS 0 550 029  7/1993  European Pat. Off. .

| | | |
|---|---|---|
| 0 575 629 | 12/1993 | European Pat. Off. . |
| 0 576 738 | 1/1994 | European Pat. Off. ........ A61F 13/15 |
| 0594123 | 4/1995 | European Pat. Off. . |
| 0 754 796 | 1/1997 | European Pat. Off. . |
| 1 084 015 | 9/1957 | Germany ............................... 156/276 |
| 44 47 152 | 7/1995 | Germany ....................... A61L 15/60 |
| 58076118 | 7/1958 | Japan . |
| 62-053719 | 8/1987 | Japan . |
| 62-074423 | 9/1987 | Japan . |
| 1-246413 | 10/1989 | Japan . |
| 5-064713 | 3/1993 | Japan . |
| 2 026 379 | 2/1980 | United Kingdom ............ D06M 9/00 |
| 2 242 142 | 9/1991 | United Kingdom .............. B03C 3/28 |
| 81/03265 | 11/1981 | WIPO . |
| 90/11784 | 10/1990 | WIPO . |
| 91/08254 | 6/1991 | WIPO . |
| 92/16681 | 10/1992 | WIPO .............................. D04H 1/42 |
| 93/06168 | 4/1993 | WIPO . |
| 93/09156 | 5/1993 | WIPO .............................. C08G 8/18 |
| 94/01068 | 1/1994 | WIPO . |
| WO 94/00166 | 1/1994 | WIPO . |
| 95/05232 | 2/1995 | WIPO . |
| 95/05501 | 2/1995 | WIPO . |
| 95/22646 | 8/1995 | WIPO . |
| 96/00093 | 1/1996 | WIPO . |
| 96/28597 | 9/1996 | WIPO . |

OTHER PUBLICATIONS

Database WPI, Section Ch, Week 8428, Derwent Publications Ltd., London, GB; Class A87, An 84–173431, XP002008760, & JP,A,59 094 621 (Unitika KK), 31 May 1984, see abstract.

Patent Abstracts of Japan, vol. 10, No. 71 (C–334), 20 Mar. 1986 & JP,A,60 209220 (Kouken K.K.), 21 Oct. 1985, see abstract.

Patent Abstracts of Japan, vol. 6, No. 191 (C–127), 30 Sep. 1982 & JP,A,57 105217 (Nitta K.K.), 30 Jun. 1982, see abstract & Chemical Abstracts, vol. 97, No. 26, 27 Dec. 1982, Columbus, Ohio, US; abstract No. 218901, "Fibrous Filtering Material", see abstract.

Patent Abstracts of Japan, vol. 11, No. 315 (C–451), 14 Oct. 1987 & JP,A,62 102809 (Mitsui Petrochem. Ind. Ltd.), 13 May 1987, see abstract & Database WPI, Section Ch, Week 8725, Derwent Publications Ltd., London, GB; Class A12, AN 87–172842 & JP,A,62 102 809 (Mitsui Petrochem. Ind. Co. Ltd.), 13 May 1987, see abstract.

Journal of Electrostatics, vol. 21, 1988, Amsterdam NL, pp. 81–98, XP002012022, P. A. Smith & G. C. East: "Generation of Triboelectric Charge in Textile Fibre Mistures, and their use as Air Filters", see document.

Database WPI, Section Ch, Week 8930, Derwent Publications, Ltd., London, GB; Class A94, AN 89–217687 XP002005648 & JP,A,01 156 578 (Showa Denko), 20 Jun. 1989, See Abstract.

"Bonding Process", IBM Technical Disclosure Bulletin, vol. 14, No. 12, May 1972.

J. van Turnhout: Topics in Applied Physics, vol. 33, Chapter 3 "Thermally Stimulated Discharge of Electrets", pp. 81–215 (1980).

J. van Turnhout: Thermally Stimulated Discharge of Polymer Electrets, Chapter 1, pp. 1–24 (1975).

G.M. Sessler: "Electronic Properties of Polymers, Chapter 3" Charge Storage, pp. 59–107.

NONWOVEN BARRIER AND METHOD OF MAKING THE SAME

This application is a continuation of application Ser. No. 08/504,209 entitled "NONWOVEN BARRIER AND METHOD OF MAKING THE SAME" and filed in the U.S. Patent and Trademark Office on Jul. 19, 1995, now abandoned. The entirety of this Application is hereby incorporated by reference.

FIELD OF THE INVENTION

The present invention is directed to bacterial and particle barrier fabrics. More particularly, the present invention is directed to nonwoven bacterial barrier fabrics for use as sterilization wrap, surgical draping, surgical gowns, cover garments, such as over-suits, and the like.

BACKGROUND OF THE INVENTION

As is generally known, surgical gowns, surgical drapes, surgical face masks and sterile wrap (hereinafter collectively "surgical articles") have been designed to greatly reduce, if not prevent, the transmission through the surgical article of liquids and/or airborne contaminants. In surgical procedure environments, such liquids sources include the gown wearer's perspiration, patient liquids, such as blood and life support liquids such as plasma and saline. Examples of airborne contaminants include, but are not limited to, biological contaminants, such as bacteria, viruses and fungal spores. Such contaminants may also include particulate material such as, but not limited to, lint, mineral fines, dust, skin squamae and respiratory droplets. A measure of a fabric's ability to prevent the passage of such airborne materials is sometimes expressed in terms of "filtration efficiency".

Many of these surgical articles were originally made of cotton or linen and were sterilized prior to their use in the operating room. In many instances, surgical articles fashioned from cotton or linen provide insufficient barrier protection from the transmission therethrough of airborne contaminants. Furthermore, these articles were costly, and, of course, laundering and sterilization procedures were required before reuse.

Disposable surgical articles, which also generally require sterilization prior to their use, have largely replaced linen surgical articles. Advances in such disposable surgical articles include the formation of surgical gowns and drapes from non-porous materials, such as films, and the formation of surgical gowns, drapes, sterile wrap, and face masks from porous nonwoven polymer materials. While surgical articles formed from non-porous materials are generally impervious to liquids and air borne contaminants, such surgical articles become, over a period of time, uncomfortable to wear. Generally, such surgical articles formed from nonwoven porous materials are more breathable and thus more comfortable to wear. However, such comfort and breathability generally occurs at the expense of liquid barrier properties and particulate barrier properties or filtration efficiency.

While the focus thus far has been directed to surgical articles, there are many other garment or over-garment applications, such as personal protective equipment applications, whose designers require both fabric comfort and filtration efficiency. Other personal protective equipment applications include, but are not limited to, laboratory applications, clean room applications, such as semiconductor manufacture, agriculture applications, mining applications, and environmental applications.

Therefore, there is a need for garment materials and methods for making the same which provide improved breathability and comfort as well as improved filtration efficiency. Such improved materials and methods are provided by the present invention and will become more apparent upon further review of the following specification and claims.

SUMMARY OF THE INVENTION

In response to the above problems encountered by those of skill in the art, the present invention provides a plasma sterilizable nonwoven material, such as nonwoven fabrics, formed from polymer fibers. The nonwoven materials of the present invention are formed by subjecting a portion of the nonwoven material to charging, for example electrostatic charging, and then plasma sterilizing, for example hydrogen peroxide plasma sterilizing, the nonwoven material. The nonwoven material may be subjected to charging followed by plasma sterilization or plasma sterilization followed by charging. The nonwoven material may also be treated with an antistatic material before or after subjecting the nonwoven material to charging.

These methods further include positioning another nonwoven material in a juxtaposed relationship with the first nonwoven material. Portions of the second nonwoven material may be subjected to charging before or after plasma sterilization. The second nonwoven material may also be treated with an antistatic material before or after being subjected to charging.

The nonwoven materials include a plasma sterilized fabric formed from fibers of a polymer wherein a portion of these fibers have been subjected to charging, for example electrostatic charging. The plasma sterilized nonwoven composition may also include an antistatic material present about portions thereof. The above nonwoven composition may further include multiple layers or plies in juxtaposed relationship. One or more of these layers or plies may be formed from dielectric polymer fibers wherein a portion of these fibers may be subjected to charging. An antistatic treatment may also be present about portions of one or more of the plies or layers.

The composition of the present invention further includes a nonwoven laminate having a first ply formed from fibers of a dielectric polymer, wherein a portion of these fibers have been subject to charging and wherein an antistatic material is present about portions of the first ply. This composition may further include a second ply formed from fibers of a polymer, wherein the polymer is positioned in a juxtaposed relationship with the first ply. The second ply may also be formed from a dielectric material and be subjected to charging.

DETAILED DESCRIPTION OF THE INVENTION

As used herein, the term "dielectric" means a material, such as a polymer, which is an electrical insulator or in which an electric field can be sustained with a minimum dissipation of power. A solid material is a dielectric if its valence band is full and is separated from the conduction band by at least 3 eV. This definition is adopted from the *McGraw-Hill Encyclopedia of Science & Technology*, 7th Edition, Copyright 1992.

As used herein, the term "nonwoven fabric" refers to a fabric that has a structure of individual fibers or filaments which are interlaid, but not in an identifiable repeating manner.

As used herein the term "spunbond fibers" refers to fibers which are formed by extruding molten thermoplastic material as filaments from a plurality of fine, usually circular capillaries of a spinnerette with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. Nos. 3,502,763 and 3,909,009 to Levy, and U.S. Pat. No. 3,542,615 to Dobo et al which are all herein incorporated by reference.

As used herein the term "meltblown fibers" means fibers formed by extruding a molten thermoplastic material through a plurality of fine, usually circular, die capillaries as molten threads or filaments into a high velocity, usually heated gas (e.g. air) stream which attenuates the filaments of molten thermoplastic material to reduce their diameter. Thereafter, the meltblown fibers are carried by the high velocity gas stream and are deposited on a collecting surface to form a fabric of randomly disbursed meltblown fibers. Meltblowing is described, for example, in U.S. Pat. No. 3,849,241 to Buntin, U.S. Pat. No. 4,307,143 to Meitner et al., and U.S. Pat. No. 4,663,220 to Wisneski et al which are all herein incorporated by reference.

The present invention provides plasma sterilizable fabrics, such as woven or nonwoven fabrics. The fabrics of the present invention are formed by subjecting a portion of the fabric to charging, for example electrostatic charging, and then plasma sterilizing, for example hydrogen peroxide plasma sterilizing, the fabric. The fabric may be subjected to charging followed by plasma sterilization or plasma sterilization followed by charging.

As such, the present invention includes compositions, and methods of making the same, which improved both the airborne contaminant barrier and filtration efficiency of both woven and nonwoven fabrics. Among the applications for such compositions and methods are included, but not limited to, applications requiring sterilizable, breathable materials having high airborne contaminant barrier properties. Such materials have application in surgical articles, such as gowns, drapes, sterile wrap and face masks, as well as other non-surgical applications such as agriculture, mining, clean room and environmental.

Polymers are well suited for the formation of fabrics, both woven and nonwoven, which are useful in the practice of the present invention. Nonwoven fabrics can be made from a variety of processes including, but not limited to, air laying processes, wet laid processes, hydroentangling processes, spunbonding, meltblowing, staple fiber carding and bonding, and solution spinning. The fibers themselves can be made from a variety of dielectric materials including, but not limited to, polyesters, polyolefins, nylons and copolymers of these materials. The fibers may be relatively short, staple length fibers, typically less than 3 inches, or longer more continuous fibers such as are typically produced by a spunbonding process.

The fabrics of the present invention may be formed from a single layer or multiple layers. In the case of multiple layers, the layers are generally positions in a juxtaposed or surface-to-surface relationship and all or a portion of the layers may be bound to adjacent layers.

As described in greater detail below, the entire thickness of the fabric may be subjected to charging. In the case of a nonwoven laminate, individual plies of the nonwoven laminate may be separately subjected to charging. Whether the entire thickness of the nonwoven laminate is subjected to charging or individual plies which ultimately form the nonwoven laminate are subjected to charging, the fibers forming at least one of the nonwoven plies are desirably formed from a variety of dielectric polymers including, but not limited to, polyesters, polyolefins, nylons and copolymers of these materials. The fibers forming the other nonwoven plies may be formed from a variety of non-dielectric materials, including, but not limited to, cellulose, glass, wool and protein polymers.

It will be further understood that in those instances when the fabric is formed from multiple layers, one or more of these layers may be formed from one or a combination of the above described dielectric materials. Additionally, one or more of these layers may be subjected to charging.

It has been found that nonwoven fabrics formed from thermoplastic based fibers and desirable polyolefin-based fibers are well-suited for the above applications. Examples of such fibers include spunbond fibers and meltblown fibers. Examples of such nonwoven fabrics formed from such fibers are the polypropylene nonwoven fabrics produced by the Assignee of record, Kimberly-Clark Corporation.

In one embodiment, the nonwoven laminate may include at least one ply formed from spunbond fibers and another ply formed from meltblown fibers, such as a spunbond/meltblown (SM) nonwoven laminate. In another embodiment, the nonwoven laminate may include at least one ply formed from meltblown fibers which is positioned between two plies formed from spunbond fibers, such as a spunbond/meltblown/spunbond (SMS) nonwoven laminate. Examples of these nonwoven laminates are disclosed in U.S. Pat. No. 4,041,203 to Brock et al., U.S. Pat. No. 5,169,706 to Collier, et al, and U.S. Pat. No. 4,374,888 to Bornslaeger which are all herein incorporated by reference. It should be noted, however, that materials other than nonwovens may be used. Examples of such other materials include wovens, films, foam/film laminates and combinations hereof, with and without nonwovens, may be used in the present invention.

The spunbond fibers may be formed from polypropylene. Suitable polypropylene for the spunbond layers are commercially available as PD-9355 from the Exxon Chemical Company of Baytown, Tex.

The meltblown fibers may be formed from polyolefin polymers, such as polypropylene and polybutylene or a blend thereof. Examples of such meltblown fibers are contained in U.S. Pat. Nos. 5,165,979 and 5,204,174 which are incorporated herein by reference. Desirably, the meltblown fibers may be formed from a blend of polypropylene and polybutylene wherein the polybutylene is present in the blend in a range from 0.5 to 20 weight percent of the blend. One such suitable polypropylene is designated 3746-G from the Exxon Chemical Co., Baytown, Tex. One such suitable polybutylene is available as DP-8911 from the Shell Chemical Company of Houston, Tex. The meltblown fibers may also contain a polypropylene modified according to U.S. Pat. No. 5,213,881 which is incorporated herein by reference.

The SMS nonwoven laminate may be made by sequentially depositing onto a moving forming belt first a spunbond ply, then a meltblown ply and last another spunbond ply and then bonding the plies together to form the laminate. Alternatively, the plies may be made individually, collected in rolls, and combined in a separate bonding step. Such SMS nonwoven laminates usually have a basis weight of from about 0.1 to 12 ounces per square yard (osy) (3 to 400 grams per square meter (gsm)), or more desirably from about 0.75 to about 5 osy (25 to 170 gsm) and still more desirably from about 0.75 to about 3 osy (25 to 100 gsm).

Methods of subjecting a material to charging, for example electrostatic charging, are well known by those skilled in the art. These methods include, for example, thermal, liquid-contact, electron beam and corona discharge methods.

Briefly, corona discharge is achieved by the application of sufficient direct current (DC) voltage to an electric field initiating structure (EFIS) in the proximity of an electric field receiving structure (EFRS). The voltage should be sufficiently high such that ions are generated at the EFIS and flow from the EFIS to the EFRS. Both the EFIS and the EFRS are desirably formed from conductive materials. Suitable conductive materials include conductive metals such as, copper, tungsten, stainless steel and aluminum.

One particular technique of subjecting the fabric to corona discharge is the technique disclosed in U.S. Pat. No. 5,401,446, which is assigned to the University of Tennessee, and is herein incorporated by reference. This technique involves subjecting the fabric to a pair of electrical fields wherein the electrical fields have opposite polarities. Each electrical field forms a corona discharge.

Desirably, plasma sterilization of the nonwoven fabric may be accomplished by subjecting the nonwoven fabric to hydrogen peroxide plasma at a sufficient pressure for a sufficient time. In those instances when the nonwoven fabric is used to wrap surgical instruments or other unsterile supplies, such items are placed in an instrument tray. The instrument tray is then generally wrapped with two juxtaposed sheets of material commonly referred to as sterilization wrap. Sterilization wrap is usually a woven or nonwoven material which, when wrapped around the tray or package contents in a certain prescribed manner, will permit the entry of sterilizing vapor/gas or other medium to sterilize the contents of the tray while denying the ingress of contaminants such as bacteria and other infection causing materials after sterilization. Once sterilization is complete, the instruments and other supplies, still wrapped, are then removed from the plasma sterilizing equipment and are stored in the wrapping material until needed. When needed, the wrapping material is removed making the instruments available for handling. The plasma sterilization cycle may vary dependent upon the type of sterilizer, the size/quantity of the items being sterilized and the composition of the chemical precursor of the active species of the plasma.

In those instances where the nonwoven fabric is used in or around flammable materials and static discharge is a concern, the nonwoven fabric may be treated with any number of antistatic materials. In these instances, the antistatic material may be applied to the nonwoven by any number of techniques including, but not limited to dipping the nonwoven into a solution containing the antistatic material or by spraying the nonwoven with a solution containing the antistatic material. In some instances the antistatic material may be applied to both the external surfaces of the nonwoven and the bulk of the nonwoven. In other instances, the antistatic material may be applied to portions of the nonwoven, such as a selected surface or surfaces thereof.

Of particular usefulness is the antistatic material known as ZELEC®, an alcohol phosphate salt product of the Du Pont Corporation. The nonwoven fabric may be treated with the antistatic material either before or after subjecting the fabric to charging. Furthermore, some or all of the material layers may be treated with the antistatic material. In those instances where only some of the material layers are treated with antistatic material, the non-treated layer or layers may be subjected to charging prior to or after combining with the antistatic treated layer or layers.

To demonstrate the attributes of the present invention, the following Examples are provided.

BACKGROUND

Kimberly-Clark manufactures a series of single sheet nonwoven laminates made from spunbond-meltblown-spunbond (SMS) plies. These materials are available in a variety of basis weights. The nonwoven samples used in Examples 1 and 2 were such single sheet laminate materials sold by Kimberly-Clark under the mark KIMGUARD® Heavy Duty Sterile Wrap. The basis weight of this material is 2.2 osy (ounces per square yard). Both spunbond plies have a basis weight of 0.85 osy and the meltblown ply has a basis weight of 0.50 osy.

The method used to subject the Samples reported in Tables I and II to electrostatic charging is described in the above referenced U.S. Pat. No. 5,401,446. The electrostatic charging was produced by using a Model No. P/N 25A - 120 volt, 50/60 Hz reversible polarity power unit (Simco Corp., Hatfield, Pa.), which was connected to the EFIS, and a Model No. P16V 120V,.25A 50/60 Hz power unit (Simco Corp., Hatfield, Pa.) which was connected to the EFRS. The EFIS was a RC-3 Charge Master charge bar (Simco. Corp.) and the EFRS was a solid, three inch diameter, aluminum roller. The electrostatic charging environment was 70° F. and 61% relative humidity. As described in the above University of Tennessee Patent Application, two sets of EFIS/EFRS are used. The voltage applied to the first set of EFIS/EFRS was 14 KV/0.0 V, respectively. The voltage applied to the second set of EFIS/EFRS was 22 KV/7.5 KV, respectively. The gap between the EFIS and the EFRS for each set was one inch.

Nelson Laboratories of Salt Lake City, Utah preformed the bacterial filtration efficiency (BFE) analysis for the Samples used in Examples 1 and 2. The procedure used to determine these BFEs is described in Nelson Laboratories' Protocol No. ARO/007C in accordance with MIL Spec 36954C, 4.4.1.1.1 and 4.4.1.2. The BFE values are reported as the percent difference between the test sample runs and the control average.

The nonwoven samples were plasma sterilized, using hydrogen peroxide as the chemical precursor of the active species of the plasma, in a STERRAD™ plasma sterilizer, model no. 100, a product of Advanced Sterilization Products, a Division of Johnson and Johnson Medical Inc.

EXAMPLE 1

Sample 1 consisted of six sheets of the above described 2.2 osy KIMGUARD® Heavy Duty Sterile Wrap containing about 0.03 percent by weight of ZELEC®, the antistatic treatment previously described, which was topically applied. The dimension of each sheet was 27"×36".

Sample 2 consisted of two sheets of the above described 2.2 osy KIMGUARD® Heavy Duty Sterile Wrap but without any ZELEC®. Both Sample 1 and 2 were subjected to electrostatic charging as described in the Background above.

Three, 10"×10"×3½" plastic surgical trays were each wrapped with two sheets of Sample 1 material. One, 10"×10"×3½" plastic surgical tray was wrapped with the two sheets of Sample 2 material. The sheet contacting the instrument tray is referred to as the "Bottom Layer" and the sheet overlying the Bottom layer is referred to as the "Top Layer".

The four double wrapped surgical trays were sterilized in a STERRAD™ plasma sterilizer. After plasma sterilization, the bacterial filtration efficiencies for the plasma sterilized Top and Bottom Layers of Sample 1 and 2 were analyzed by Nelson Laboratories. Table I reports the data for the plasma sterilized Sample 1, Top and Bottom Layers and Table II reports the data for the plasma sterilized Sample 2, Top and Bottom Layers. The data reported in Tables I and II are the average of eleven measurements taken from different locations on each layer of material.

TABLE I

| 2.2 osy KIMGUARD ® BFE% Charged With ZELEC ® | |
|---|---|
| Top Layer | Bottom Layer |
| 95.2 +/− 0.93 | 97.8 +/− 0.53 |
| 94.8 +/− 0.76 | 98.7 +/− 0.41 |
| 95.6 +/− 0.84 | 98.7 +/− 0.22 |

TABLE II

| 2.2 osy KIMGUARD ® BFE% Charged Without ZELEC ® | |
|---|---|
| Top Layer | Bottom Layer |
| 94.3 +/− 1.98 | 98.2 +/− 0.66 |

EXAMPLE 2

Sample 3 consisted of six sheets of the above described 2.2 osy KIMGUARD® Heavy Duty Sterile Wrap containing about 0.03 percent by weight of ZELEC®, the antistatic treatment previously described, which was topically applied. The dimension of each sheet was 27"×36".

Sample 4 consisted of two sheet of the above described 2.2 osy KIMGUARD® Heavy Duty Sterile Wrap but without any ZELEC®. Samples 3 and 4 were not subjected to electrostatic charging. Three, 10"×10"×3½" plastic surgical trays were each wrapped with two sheets of Sample 3 material. One, 10"×10"×3½" plastic surgical tray was wrapped with the two sheets of Sample 4 material. The sheet contacting the instrument tray is referred to as the "Bottom Layer" and the sheet overlying the Bottom layer is referred to as the "Top Layer".

The four double wrapped surgical trays were sterilized in the STERRAD™ plasma sterilizer. After plasma sterilization, the bacterial filtration efficiencies for the plasma sterilized Top and Bottom Sample Layers were analyzed by Nelson Laboratories. Table III reports the data for the plasma sterilized Sample 3, Top and Bottom Layers and Table IV reports the data for the plasma sterilized Sample 4, Top and Bottom Layers. The data reported in Tables III and IV are the average of eleven measurements taken from different locations on each layer of material.

TABLE III

| 2.2 osy KIMGUARD ® BFE% With ZELEC ® | |
|---|---|
| Top Layer | Bottom Layer |
| 90.7 +/− 1.42 | 93.1 +/− 1.48 |
| 91.5 +/− 1.56 | 92.0 +/− 1.53 |
| 92.4 +/− 1.56 | 92.5 +/− 0.67 |

TABLE IV

| 2.2 osy KIMGUARD ® BFE% Without ZELEC ® | |
|---|---|
| Top Layer | Bottom Layer |
| 88.0 +/− 2.92 | 89.6 +/− 1.75 |

As demonstrated by the above Examples, the barrier properties of plasma sterilized non-woven materials are improved when these materials are subjected to charging, for example electrostatic charging. It will be further observed that the barrier properties of a plasma sterilized antistatic treated non-woven materials are improved when these materials are subjected to charging, for example electrostatic charging.

While the invention has been described in detail with respect to specific embodiments thereof, it will be appreciated that those skilled in the art, upon attaining an understanding of the foregoing, may readily conceive of alterations to, variations of and equivalents to these embodiments. Accordingly, the scope of the present invention should be assessed as that of the appended claims and any equivalents thereto.

What is claimed is:

1. A method of manufacturing a fabric comprising plasma sterilizing a charged fabric.

2. The method of claim 1 wherein the fabric is plasma sterilized prior to being subjected to charging.

3. The method of claim 1 wherein the fabric is subjected to charging prior to being plasma sterilized.

4. The method of claim 1 wherein the charging is electrostatic charging.

5. The method of claim 1 wherein the fabric is a non-woven fabric.

6. The method of claim 1 wherein the fabric comprises first and second nonwoven fabrics positioned in juxtaposed relationship.

7. The method of claim 6 wherein the first and second nonwoven fabrics are positioned in juxtaposed relationship after the charging step.

8. The method of claim 7 wherein the first nonwoven fabric is subjected to charging and the second nonwoven fabric is not subjected to charging.

9. The method of claim 6 wherein the first nonwoven fabric is treated with an antistatic material.

10. The method of claim 9 wherein the second nonwoven fabric is treated with an antistatic material.

11. A method of manufacturing a nonwoven fabric comprising plasma sterilizing a charged nonwoven fabric and treating the nonwoven fabric with an antistatic material.

12. The method of claim 11 wherein the nonwoven fabric is treated with the antistatic material prior to being charged.

13. The method of claim 11 wherein the nonwoven fabric is charged prior to being treated with the antistatic material.

14. The method of claim 11 wherein the fabric has been electrostatically charged.

15. The method of claim 11 wherein the nonwoven material is a nonwoven laminate comprising first, second and third nonwoven plies.

16. The method of claim 15 wherein at least one of the plies has been subjected to charging.

17. The method of claim 16 wherein the second nonwoven ply is subjected to charging and the first and third nonwoven plies are not subjected to charging.

18. A plasma sterilized fabric that has been subjected to charging.

19. The plasma sterilized fabric of claim 18 wherein the fabric comprises first and second nonwoven fabrics positioned in juxtaposed relationship.

20. The plasma sterilized fabric of claim 18 wherein the fabric has been treated with an antistatic material.

21. The plasma sterilized fabric of claim 20 wherein the fabric is a nonwoven laminate comprising first and second nonwoven plies.

22. A charged, plasma sterilized fabric having a bacterial filtration efficiency of at least 94%.

23. The charged fabric of claim 22 wherein the fabric is an electrostatically charged fabric.

24. The charged fabric of claim 22 wherein the fabric is a nonwoven fabric.

25. The charged fabric of claim 24 wherein the nonwoven fabric comprises two outer layers separated by an intermediate layer.

26. The charged fabric of claim 25 wherein the two outer layers are spunbond nonwoven layers and the intermediate layer is a meltblown layer.

27. The charged fabric of claim 22 containing antistatic material.

28. A fabric prepared by a process comprising sterilizing a charged fabric by plasma sterilization.

29. The fabric of claim 28 wherein the charged fabric is an electrostatically charged fabric.

30. The fabric of claim 28 wherein the charged fabric is a nonwoven fabric.

31. The fabric of claim 30 wherein the nonwoven fabric comprises two outer layers separated by an intermediate layer.

32. The fabric of claim 31 wherein the two outer layers are spunbond nonwoven layers and the intermediate layer is a meltblown layer.

33. The fabric of claim 28 wherein the process further comprises treatment with an antistatic material.

* * * * *

UNITED STATES PATENT AND TRADEMARK OFFICE
CERTIFICATE OF CORRECTION

PATENT NO. : 5,830,810  
DATED : November 3, 1998  
INVENTOR(S) : Bernard Cohen

Page 1 of 2

It is certified that error appears in the above-identified patent and that said Letters Patent is hereby corrected as shown below:

Title page, item 56, under References Cited, U.S. Patent Documents, the following patents should be added:

| Patent No. | Date | Inventor | Class | Subclass |
|---|---|---|---|---|
| 813,063 | 02/20/06 | Sutton et al. | | |
| 859,998 | 07/16/07 | Wentworth | | |
| 924,032 | 06/08/09 | Blake et al. | | |
| 1,222,305 | 04/10/17 | Kraus | | |
| 1,297,159 | 03/11/19 | Hedberg | | |
| 1,355,477 | 10/12/20 | Howell | | |
| 2,106,865 | 02/01/38 | Bantz et al. | 209 | 127 |
| 2,217,444 | 10/8/40 | Hill | 91 | 18 |
| 2,328,577 | 09/07/43 | Oglesby | 117 | 17 |
| 2,398,792 | 04/23/46 | Johnson | 209 | 127 |
| 2,378,067 | 03/13/56 | Cook, Jr. | 209 | 127 |
| 3,012,668 | 12/12/61 | Fraas | 209 | 127 |
| 3,341,007 | 09/12/67 | Mayer et al. | 209 | 2 |
| 3,380,584 | 04/30/68 | Fulwyler | 209 | 3 |
| 3,402,814 | 09/24/68 | Morel et al. | 209 | 127 |
| 3,581,886 | 06/01/71 | Singewald et al | 209 | 9 |
| 4,305,797 | 12/15/81 | Knoll et al. | 204 | 180R |
| 4,357,234 | 11/02/82 | Inculet et al. | 209 | 127B |
| 4,363,723 | 12/14/82 | Knoll et al. | 209 | 128 |
| 4,374,727 | 02/22/83 | Takahashi et al | 209 | 127B |

UNITED STATES PATENT AND TRADEMARK OFFICE
CERTIFICATE OF CORRECTION

PATENT NO. : 5,830,810  
DATED : November 3, 1998  
INVENTOR(S) : Bernard Cohen

It is certified that error appears in the above-identified patent and that said Letters Patent is hereby corrected as shown below:

| | | | | |
|---|---|---|---|---|
| 4,514,289 | 04/30/85 | Inculet | 209 | 127.3 |
| 4,547,420 | 10/15/85 | Krueger et al. | 428 | 229 |
| 4,699,823 | 10/13/87 | Kellenberger et al. | 428 | 219 |
| 4,729,371 | 03/08/88 | Krueger et al. | 128 | 206.19 |

Signed and Sealed this

Seventeenth Day of August, 1999

Attest:

Q. TODD DICKINSON

*Attesting Officer*    *Acting Commissioner of Patents and Trademarks*